United States Patent [19]

O'Neill

[11] Patent Number: 5,098,196
[45] Date of Patent: Mar. 24, 1992

[54] CIRCUIT FOR HEATING AND SENSING WITH A SINGLE ELEMENT

[75] Inventor: Michael J. O'Neill, Ridgefield, Conn.

[73] Assignee: The Perkin-Elmer Corporation, Norwalk, Conn.

[21] Appl. No.: 637,392

[22] Filed: Jan. 4, 1991

[51] Int. Cl.$^5$ .................. G01N 25/00; H05B 1/02
[52] U.S. Cl. ............................... 374/11; 219/497
[58] Field of Search ............... 374/11, 10, 45, 14; 219/412, 497

[56] References Cited

U.S. PATENT DOCUMENTS

| | | |
|---|---|---|
| 3,263,484 | 8/1966 | Watson et al. |
| 3,360,993 | 1/1968 | MacMillan ............... 374/10 X |
| 3,527,923 | 9/1970 | O'Neill . |
| 3,675,465 | 7/1972 | Sommer et al. ............... 374/11 |
| 4,277,672 | 7/1981 | Jones ............... 219/499 X |
| 4,636,619 | 1/1987 | Sugimori ............... 219/499 X |
| 4,777,350 | 10/1988 | Crockett ............... 219/497 |

Primary Examiner—Daniel M. Yasich
Attorney, Agent, or Firm—H. S. Ingham; E. T. Grimes

[57] ABSTRACT

A circuit for differential calorimetry includes a pair of resistance elements in a bridge circuit. Separate DC heating currents are effected in each element by high impedance current sources. An AC voltage is applied to the bridge. In measuring AC differental voltage between the elements, the DC is filtered out. The filtered AC differential voltage is fed back to effect a current differential between the heating currents to null the differential temperature causing the differential voltage. A similarly filtered average AC voltage on the elements is compared with a reference voltage, and the resulting error voltage is fed back to control the average of the heating currents. A very high impedance current source includes a voltage-current transducer with an output of a heating current passed through a monitor resistor, with matched resistances from both sides of the monitor connected back to positive and negative inputs to the transducer, and a control voltage applied across the inputs.

25 Claims, 3 Drawing Sheets

CIRCUIT FOR HEATING AND SENSING WITH A SINGLE ELEMENT

This invention relates to calorimetric analytical instruments, and particularly to differential scanning calorimetry with a single element associated with each sample material for both heating the sample and sensing its temperature.

BACKGROUND OF THE INVENTION

Differential thermal analysis (DTA) is an old and well-known method for the analysis of materials. Basically, the method consists of applying heat simultaneously to a sample material and a reference material. As the sample material goes through various physical and chemical changes, such as crystallization, melting, freezing, oxidation, etc., its temperature is affected by the changes in internal energy. In simple DTA the differences in temperature between the sample and reference are recorded and, from this data, calculations may be made for determining the internal energy changes occurring in the sample. In a more sophisticated instrument, such as disclosed in U.S. Pat. No. 3,263,484 of the present assignee, a feedback circuit utilizes the differential temperature measurement to effect a current differential, in which case a differential power is computed to determine changes in internal energy.

In prior heating and temperature sensing arrangements, such as taught in the aforementioned patent, the sample has been heated by applying electrical energy to a resistive heating element while the sample temperature is sensed by an independent resistive sensing element or by a thermocouple element. One arrangement employs a relatively small furnace adapted to receive a sample container and includes resistive heating and temperature sensing elements positioned in the furnace relative to the sample container. In another form, the temperature sensing element comprises a thermocouple positioned near but generally spaced away from the furnace. These arrangements suffer from one or more defects including heater-sensor thermal lag, electrical leakage, relatively large sample holder capacity, difficulties in furnace fabrication, a large number of electrical leads, and relative complexity and cost of associated circuitry.

Generally each sample being tested or compared in an instrument is placed in a cup or crucible having two resistance elements. One element has a heating current passed through it to heat the sample, the heating current being controlled by comparison with a setpoint. The other resistance element, which may be the same type of resistance coil as the first, is utilized for sensing temperature by measurement of changes in resistance with temperature.

U.S. Pat. No. 3,527,923, also of the present assignee, discloses the use of a single element for both heating and sensing. A special circuit alternates between sensing the element voltage and a preset voltage, and feeds back a square wave representing the difference between these voltages to regulate average heating current in the element. This circuit is not adapted to sensing and utilizing temperature difference between elements for two samples.

SUMMARY OF THE INVENTION

An object of the invention is to provide a novel circuit arrangement for generating heat and measuring temperature simultaneously with a single resistance element for each sample material in an analytical instrument. Another object is to provide a novel circuit arrangement for providing current to generate heat in two resistance elements, each element being associated with a separate sample material, and simultaneously measuring the differential voltage representing a differential temperature between the elements. A further object is to provide feedback of the differential temperature to control the heating currents so as to null the temperature difference, and to present the incremental power needed. An additional object is to additionally provide feedback of the average temperature to regulate the average heating currents. Yet another object is to provide an improved circuit for providing current at very high impedance.

The foregoing and other objects are achieved by a circuit arrangement with a single resistance element having an element resistance responsive to temperature. The circuit comprises first current means for effecting a heating current at a first frequency (such as a DC) in the resistance element, second current means for effecting a sensing current at a second frequency (such as AC) in the resistance element so as to induce a sensing voltage responsive to the element resistance, and measuring means for measuring voltage across the resistance element. The sensing current is effected simultaneously with the heating current. The measuring means include filtering means for filtering out the first frequency so as to produce a filtered signal representative of the sensing voltage. The filtered signal thereby provides a measure of temperature of the resistance element. Where the resistance element is proximate a sample material, the heating current heats the sample material, and the filtered signal simultaneously provides a measure of temperature of the sample material.

In an embodiment for heating and comparing two sample materials, a circuit arrangement comprises a pair of resistance elements each having a corresponding element resistance responsive to temperature, first current means for effecting at a first frequency separate heating currents in each of the resistance elements, second current means for effecting at a second frequency separate sensing currents in each of the resistance elements so as to induce on each a corresponding sensing voltage responsive to element resistance, and measuring means for measuring a voltage differential between the sensing voltages. The sensing currents are effected simultaneously with the heating currents. The measuring means include filtering means for filtering out the first frequency so as to produce a filtered signal representative of the voltage differential. The filtered signal thereby provides a measure of differential temperature between the resistance elements and the associated sample materials. Where there is a difference in heating between the sample materials, and therefore between resistance elements, to thereby effect the voltage differential in producing the filtered signal, the first current means is made to be receptive of the filtered signal to generate a corresponding current differential between the heating currents, so as to compensate for the difference in heating and thereby reduce the voltage differential.

In a prefered embodiment, the sensing voltages are averaged and filtered of the first frequency to produce a feedback signal which is compared with a reference signal to generate an error signal. The current source is then receptive of the error signal and the filtered signal to effect the heating currents. One of the heating currents is the sum of a base current and a positive current increment, and the other is the sum of the base current and a negative current increment. The base current represents the error signal, and each current increment is equal in magnitude to half of the current differential.

The apparatus may further include means for computing a multiplication product of the current differential and an average of the heating voltages, as a measure of incremental power utilized to compensate for the difference in heating. Preferably the first current means comprises a high impedance current source for each of the heating currents. In a specific aspect the current source comprises, for each associated resistance element, a voltage-to-current transducer and associated resistors with specified relationships. The transducer has a current output terminal, a positive input terminal with a first input resistor extending therefrom, and a negative input terminal with a second input resistor extending therefrom, the first and second input resistors being substantially equal. A control voltage is applied across the first and second input resistors. A monitor resistor is connected between the output terminal and a current output point. A first feedback resistor is connected between the output terminal and the negative input terminal, and a second feedback resistor is connected between the output point and the positive input terminal. The first and second feedback resistors are substantially equal. The feedback resistors and the input resistors are each substantially greater than the monitor resistor. The current output point is connected to the associated resistance element, or other load, so as to effect the current therein proportional to the control voltage.

DETAILED DESCRIPTION OF THE INVENTION

Figure 1:
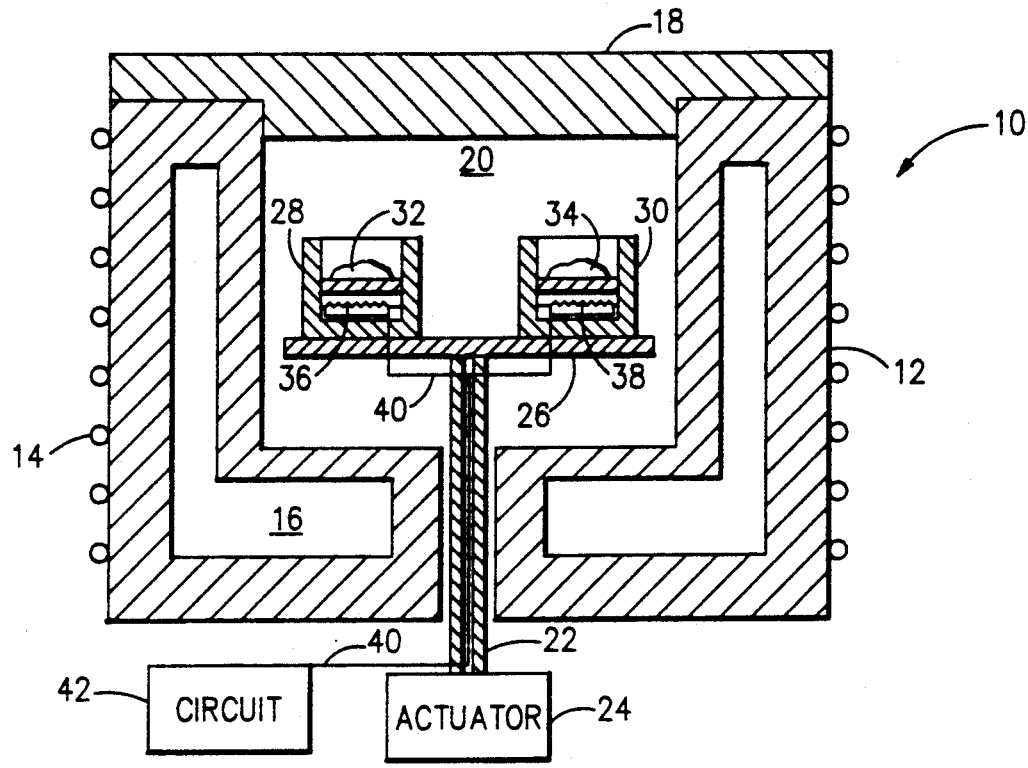
FIG. 1 is a simplified vertical section of a portion of an analytical instrument incorporating the invention.

FIG. 1 illustrates a portion 10 of an analytical instrument such as a differential scanning calorimeter (DSC), for example a Perkin-Elmer DSC-7 type of calorimeter, incorporating the invention. A heating block 12 of silver or other suitable heat-sink material is maintained at a nominal temperature by a heating coil 14 on the outside and channels 16 for a flowing cooling gas through the block. A cover 18 of similar material sits on the block, and the enclosed chamber 20 may contain an oxidative, inert or other atmosphere. A support rod 22 extends vertically into the chamber from a linear actuator 24 or other support outside the block, and holds a platform 26 of platinum or other suitable material resistant to the environment in the chamber. A pair of sample cups 28,30 is mounted on the platform. Sample materials are placed in the cups, one sample 32 generally being a standard and the other sample 34 having some thermal characteristic to be compared with that of the standard. The aforementioned features are generally conventional for a DSC.

According to the present invention each sample cup has a single dedicated resistance element 36,38 proximate the associated sample, each element functioning both for heating the sample material and measuring its temperature. Each element has an element resistance that varies with, i.e. is responsive to, temperature. The single elements are used in place of two such elements for each sample in a conventional DSC. Each element may, however, be the same type of resistance element such as a flat platinum coil used in a conventional instrument, typically ranging from about 10 ohms up to 35 ohms over a temperature range of 0° C. to 700° C. Leads 40 from the elements are fed down through the support rod 22 and led out to circuitry 42.

Figure 2:
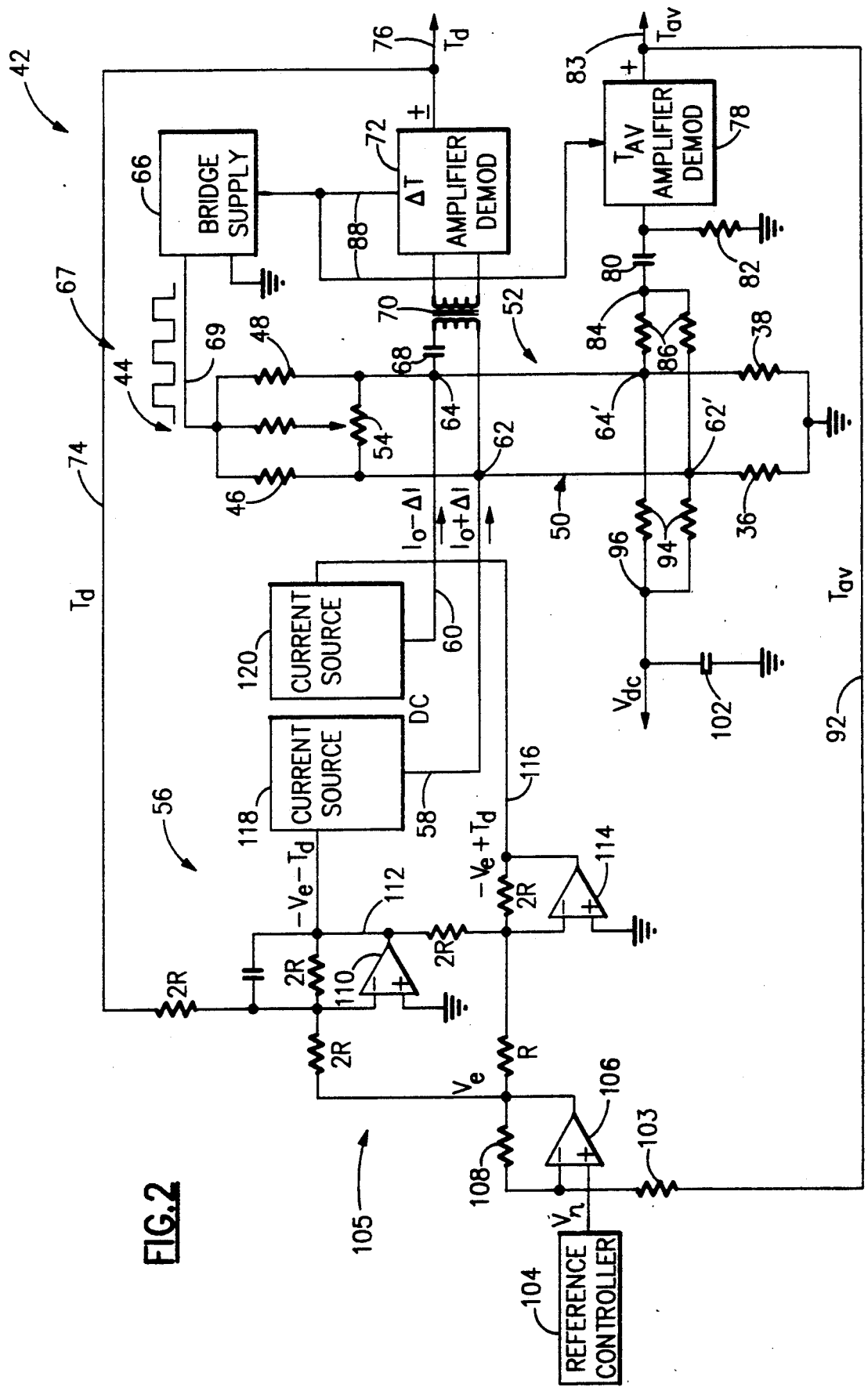
FIG. 2 is a schematic diagram of a circuit according to the invention.

FIG. 2 is a diagram illustrating circuitry 42 of the invention. A bridge circuit 44 is formed in part by the resistance elements, 36,38 which should have matched element resistances. A pair of matched series resistances 46,48 of much higher resistance than the elements, such as 500 ohms, are connected in series with the elements to form two voltage dividers 50,52 that are connected in parallel to form the bridge. A balance potentiometer 54 of high resistance is advantageously bridged between these resistances. In combination with a voltage source 66, the bridge constitutes a current means 67 for applying a sensing current through each element.

For each pair of elements a selected heating current is generated and directed from a first current means 56 via lines 58,60 to associated connecting points 62,64 respectively between the series resistances and the resistance elements. Each separate heating current generates heat in its associated element 36,38 which thereby provides heat to the associated sample material 32,34 in the cup (FIG. 1). The heating currents are effected at a first frequency which advantageously is substantially zero, i.e. direct currents preferably are used for heating. These currents constitute the principal temperature controls for the sample materials. Conventional feedback of average sample holder temperature forces the block temperature to follow, via the outer coil 14 and the cooling gas in the channels 16.

In the second current means 67, a bridge voltage supply 66 applies a voltage on line 69 at a second frequency across the combined resistances in parallel. This frequency is significantly different than the first frequency so that associated signals may be filtered from each other. In the preferable case of the first frequency being zero (DC heating currents), the second frequency should be at least 100 Hz, for example 6 KHz. The AC waveform is any convenient wave such as a sine wave or, as shown, a square wave. The applied voltage effects the sensing current which induces a sensing voltage across each of the resistance elements 36,38 and responsive to the resistance thereof. With sufficiently high series resistances 46,48, there is generated in each resistance element 36,38 the corresponding sensing current which, preferably, is substantially less than the heating current so as not to contribute significantly to the heating of the elements. Typical values are 100 milliamperes for each heating current, and 5 milliamperes for each sensing current.

A filtering means comprising a coupling capacitor 68 and a transformer 70 are attached between the two connecting points 62,64 so as to high pass filter out the DC and pass through an AC voltage differential between these points, the differential being the difference between the sensing voltages across the resistance elements. A measuring means including a conventional amplifier and demodulator unit 72 receives and amplifies the filtered voltage at the second frequency, and provides a filtered (DC) signal Td on a line 74 proportional to the differential voltage.

The amplifier/demodulator 72 may be the same type of unit used for similar purpose in the aforementioned model DSC-7 calorimeter. As the resistances of the elements 36,38 are generally proportional to their respective temperatures, the filtered signal $T_d$ from this unit represents the temperature difference between the elements, and thereby between the proximate sample materials. In particular, if some differential heating source exists in one of the samples, such as an exothermic or endothermic reaction in the material, this will be manifested as a temperature differential. An outgoing line 76 provides for a readout of the temperature differential.

Another similar amplifier/demodulator 78 after a filter capacitor 80 and a high grounding resistance 82 is utilized to filter the DC and provide a signal on line 83 representing average temperature $T_{av}$ of the elements. In this case average voltage is detected at a contact point 84 between a pair of matched resistors 86, e.g. 1K, taken respectively from the connecting points 62',64' (respectively equivalent to points 62,64).

Lines 88 between the bridge supply and the amplifier/demodulator circuits are connected conventionally to couple the frequencies for phase-sensitive demodulation.

The foregoing circuitry is directed to a differential calorimeter having two resistance elements. It will be appreciated that concepts of the invention also can be utilized with a single element, for example where a single sample material is to be heated and monitored. Only a single heating current is needed, and is fed into a voltage dividing circuit substantially the same as one side of the bridge 44 (FIG. 2). An AC sensing voltage is measured across the element, with filtering out of the frequency of the heating current which preferably is DC. The filtered signal is a measure of the temperature of the element and its associated sample material. The signal may be fed back to regulate the heating current, for example to maintain constant temperature.

Returning to the bridge circuity of FIG. 2, an average DC voltage $V_{dc}$ is taken from a point 96 between a similar pair of matched resistors 94 from the connecting points 62',64'. The AC is filtered out by a low pass filter comprising a capacitor 102 to ground. This voltage is used for computation of differential power as explained subsequently below.

The current means 56 may be simply a regulated voltage supply. However, in a preferred embodiment a high impedance current controller is utilized as a further means of separating the heating and sensing functions, i.e. preventing interference between the heating and sensing currents and associated circuits. Objectives for the current controller are to control by feedback an average or base heating current to each element, for average temperature control, and also to provide a current differential as needed to null any difference between temperatures of the resistance elements caused by a thermal difference between sample materials.

With a feedback loop 92, the average voltage signal $T_{av}$ representing average temperature is applied through a resistance 103 to a control section 105 of the current controller 56. Less preferably, the average DC voltage $V_{dc}$ may be used for this feedback. A reference DC signal voltage $V_r$ is taken from a controller 104 which is set or programmed as desired to hold or change the average temperature. This controller may incorporate a programmed non-linearity to the extent necessary to compensate for nonlinearites in the circuit. The reference voltage $V_r$ and the average temperature signal $T_{av}$ are compared by an operational amplifier (op amp) 106 with feedback 108 of 200K to yield an error voltage $V_e$. The error voltage is positive, e.g. $V_r$ being about 2 to 8 volts and $T_{av}$ being similar but larger.

The filtered signal voltage $T_d$ representing differential temperature is also fed on line 74 back to the control means 105. The error voltage $V_e$ and the filtered signal $T_d$ are added together and inverted by an op amp 110 to produce a first signal $-V_e-T_d$ on a line 112. To this latter signal the error voltage $V_e$ is again added and the combination is inverted with an op amp 114 to produce a second signal $-V_e+T_d$ on a line 116. The "R" resistors in these op amp circuits are selected with proportions as shown in the figure, R suitably being 10K. Other resistors designated "2R" have twice the resistance of R. The first and second signals are fed to respective controlled current sources 118,120 in the heating means to effect proportionate, modified heating currents via lines 58,60 to the respective resistive heating elements. As high impedance current control is preferable over voltage control, a pair of constant-current circuits is utilized for the sources 118,112 with respective input from the two signals. The heating current on line 58 is the sum of a base current $I_o$ and a positive current increment $\Delta I$, and the heating current on line 60 is the sum of the base current and a negative current increment $-\Delta I$. Each current increment is equal in magnitude to half of the current differential needed to null any difference between temperatures of the resistance elements 36,38.

Figure 3:
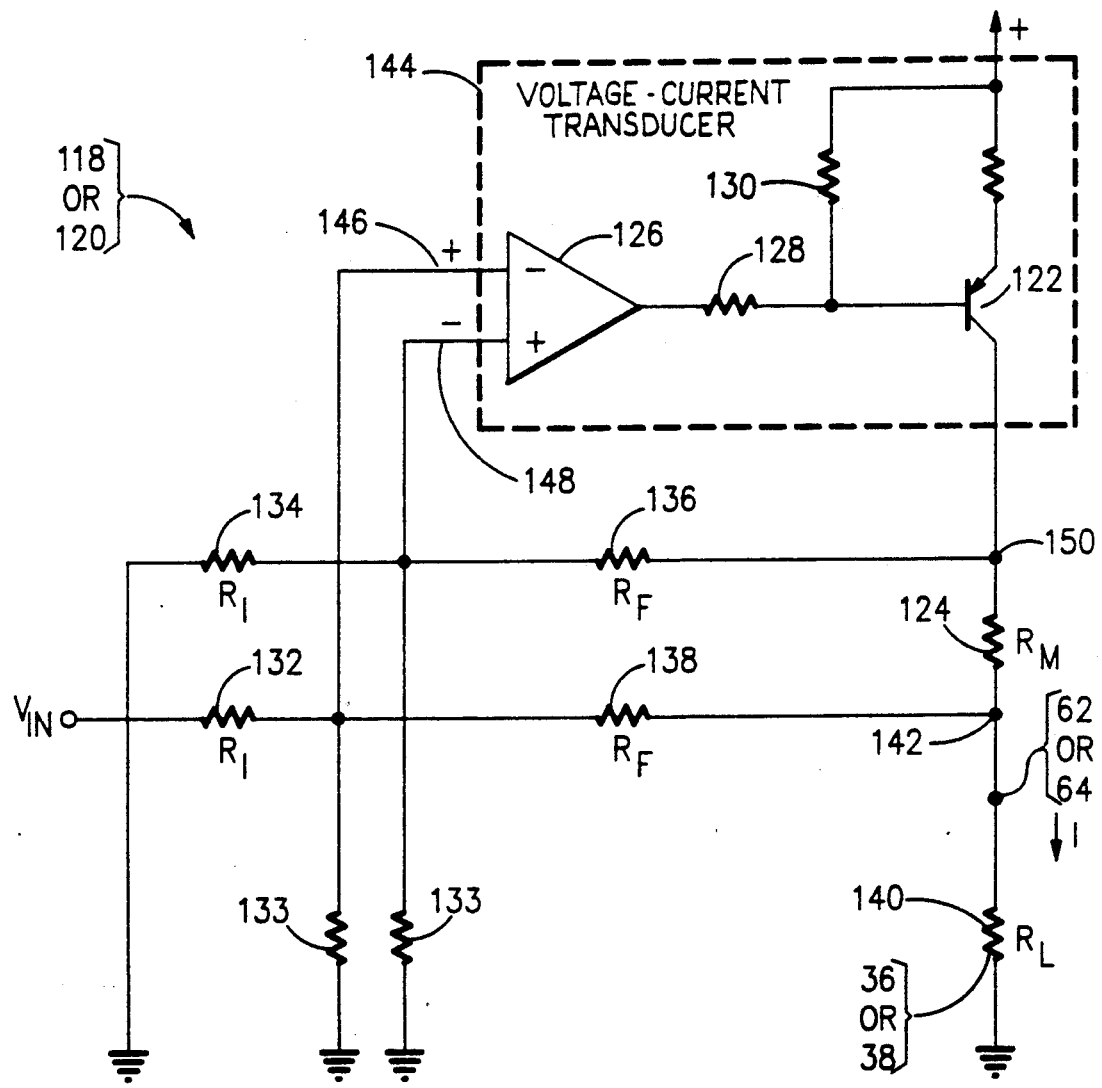
FIG. 3 is a schematic diagram of a circuit for a current source according to the invention.

According to a preferred embodiment of the invention, a modified transistor circuit of the type shown in FIG. 3 is utilized for the circuits 118 and 120. A PNP transistor 122 with a positive voltage on its emitter has on its collector a monitor resistor 124 of about one ohm. Input to the transistor base is from an op amp 126 output via a 5K resistor 128 biased by the emitter voltage via a resistor 130. Each input of the op amp has an optional resistance 133 to a base terminal (generally ground) these being matched resistors. The first or second signal, designated in FIG. 3 as $V_{in}$, ($V_{in}$ being either $-V_c-T_d$ or $V_c+T_d$ respectively from line 112 or 116 in FIG. 2) is applied to the inverting input of the op amp via a first input resistance 132, and the non-inverting input of the op amp is further grounded through a second input resistance 134 matched to the first. For more general use of this circuit, the second input need not be grounded directly, and $V_{in}$ is applied across the input resistors; in such case $V_{in}$ may be the difference between respective voltages applied with respect to ground to the first and second input resistors. The transistor collector side of the monitor resistor 124 is connected via a first feedback resistance 136 to the non-inverting input of the op amp, and the other side of the monitor resistor is connected via a second feedback resistance 138 of the same value (within about 0.1%) to the inverting input. Thus the voltage across the monitor is measured and applied accurately across the op amp inputs.

The input, feedback and (if used) grounding resistances should be much higher than the value $R_M$ of the monitor resistance 124. For example the feedback resistances $R_F$ are each 10K and the input resistances $R_I$ are half of $R_F$. The output current I in a load resistance 140 at a current output point 142 from the monitor 124 is determined from the formula $I/V_{in}=R_F/R_MR_I$. Thus $V_{in}$ functions as a control voltage. The load resistance 140 is, in the present case, either of the resistance elements 36 or 38 (FIG. 2).

With reference also to FIG. 2, the current I from point 142 (FIG. 3) is directed to point 62 or 64 and respective resistance element 36 or 38, the latter serving as the load 140 for the current source circuit of FIG. 3. Thus, except for showing duplication of the point 62 or 64 and respective resistance elements 36 or 38, the circuitry of FIG. 3 performs as each of the current sources 118 and 120 of FIG. 2.

The portion of circuit within the box 144 (dashed lines) is a conventional high impedance current source having a typical impedance of about 100K. The associated circuitry of FIG. 3, explained above according to an embodiment of the present invention, increases the impedance to megohms even at frequencies up to 100 KHz. The very high impedance is advantageous to the single element heating/sensing aspect of the invention, to minimize cross coupling of the heating and sensing functions.

In a broader aspect of FIG. 3 the box 144 represents any conventional or desired voltage-to-current transducer, for example another high impedance source substituting for the transistor-op amp combination shown. Thus, broadly for the transducer 144, there is a positive input 146 (achieved in FIG. 3 by the inverting op amp input), a negative input 148 (achieved by the non-inverting input) and a current output point 150 to the monitor 124. A simpler version may utilize a simple op amp for the transducer; in such case the non-inverting input of the op amp is utilized for the positive input for the transducer, and the inverting input for the negative input.

The monitor current via point 142 is the heating current fed to the corresponding resistance element. The current applied to one element is a base current plus half of the current differential, and the current to other element is base minus half of the differential.

As taught in the aforementioned U.S. Pat. No. 3,236,484, the differential power applied to the resistance elements is a useful measure in a DSC of the differential heating or cooling in a test sample compared with the standard. In the present case the differential power is the multiplication product of the average voltage and the differential current.

Figure 4:
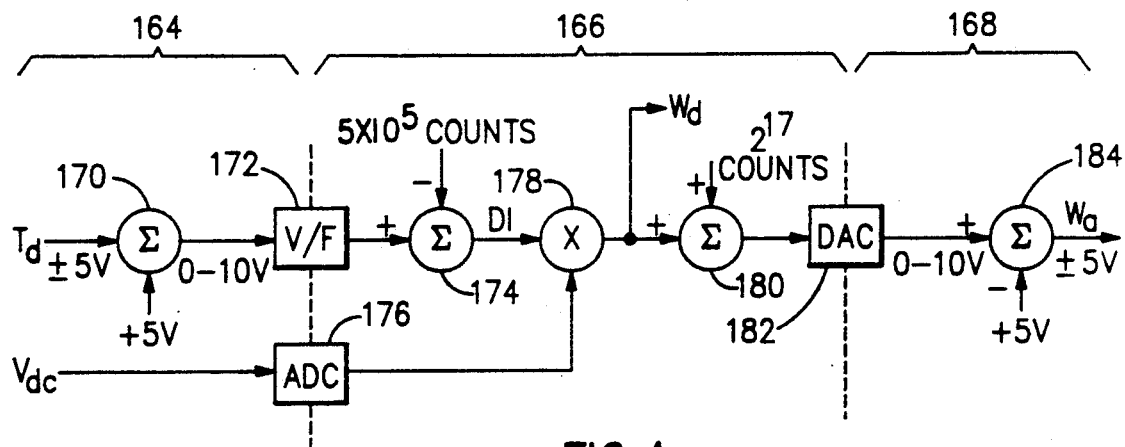
FIG. 4 is a schematic diagram of a circuit for calculating differential power applied by the circuit of FIG. 2.

A suitable circuit 162 for computing differential power is shown in FIG. 4. There are three sections, a first analog section 164, an digital section 166 and a second analog section 168. The digital section is any conventional type with analog-digital converters and, for example may be a Perkin-Elmer TAC-7 digital unit used in the DSC-7 system.

In the first analog section 164, the filtered signal $T_d$ which may be plus or minus up to about 5 volts, is summed 170 with 5 volts to produce an always positive signal. At the digital input this analog voltage is converted with a voltage/frequency (V/F) converter 172 to a frequency, e.g. up to 5 mHz, and $5*10^5$ counts per second (Hertz) is subtracted at 174 (to remove the analog 5 volts added) to provide a digital difference signal DI. Meanwhile the average voltage $V_{dc}$ is similarly with an analog/digital converter (ADC) converted 176 and then digitally multiplied 178 with the difference signal. The result is a digital measure of differential power $W_d$ which may be used as such in computer analyses and display. Optionally, e.g. for an analog recorder readout, the result also is added 180 with an offset of $2^{17}$ converted with a digital/analog converter 182 back to an analog voltage with the same range as the input voltage, and 5 volts is subtracted 184 to provide a plus/minus analog differential power output $W_a$.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. A circuit arrangement for providing heat and measuring temperature in an analytical instrument, comprising a resistance element having an element resistance responsive to temperature, first current means for effecting a heating current at a first frequency and being connected to direct the heating current through the resistance element and thereby heat the resistance element, second current means for effecting a sensing current at a second frequency and being connected to direct the sensing current through the resistance element so as to induce a sensing voltage responsive to the element resistance and thereby to temperature of the resistance element, and measuring means connected to the resistance element for determining a measured voltage on the resistance element, wherein the sensing current is effected simultaneously with the heating current, and the measuring means includes filtering means for filtering out the first frequency from the measured voltage so that the measured voltage is a filtered signal representative of the sensing voltage, whereby the filtered signal is representative of the temperature of the resistance element.

2. The apparatus of claim 1 wherein the resistance element is positionable proximate a sample material, such that the resistance element with the heating current heats the sample material, and the filtered signal provides a measure of temperature of the sample material.

3. The apparatus of claim 1 wherein the first frequency is substantially zero such that the heating current is substantially DC, and the second frequency is at least about 100 Hz.

4. The apparatus of claim 1 wherein the second current means comprises a voltage dividing circuit that includes the resistance element.

5. The apparatus of claim 1 wherein the sensing current is substantially less than the heating current.

6. The apparatus of claim 1 wherein the filtered signal is fed back to the first current means to regulate the heating current.

7. The apparatus of claim 1 wherein the first current means comprises a high impedance current source for the heating current.

8. The apparatus of claim 7 wherein the current source comprises:

a voltage-to-current transducer having a current output terminal, a positive input terminal with a first input resistor extending therefrom, and a negative input terminal with a second input resistor extending therefrom, the first and second input resistors being substantially equal;

control means for applying a control voltage across the first and second input resistors;

a monitor resistor connected between the output terminal and a current output point;

a first feedback resistor connected between the output terminal and the negative input terminal; and a second feedback resistor connected between the output point and the positive input terminal, the first and second feedback resistors being substantially equal, the feedback resistors and the input resistors each being substantially greater than the monitor resistor, and the current output point being connected to the element resistance so as to effect the heating current therein, whereby the heating current is responsive to the control voltage.

9. The apparatus of claim 8 wherein the control means is receptive of the filtered signal to generate the control voltage in response to the filtered signal.

10. A circuit arrangement for providing heat and measuring differential temperature in an analytical instrument, comprising a pair of resistance elements each having a corresponding element resistance responsive to temperature, first current means for effecting at a first frequency separate heating currents and being connected to direct a corresponding one of the heating currents through each of the resistance elements and thereby heat the resistance elements, second current means for effecting at a second frequency separate sensing currents and being connected to direct a corresponding one of the heating currents through each of the resistance elements so as to induce on the resistance elements corresponding sensing voltages each being responsive to element resistance and thereby to temperature of a corresponding resistance element, and measuring means connected for measuring a voltage differential between the sensing voltages, wherein the sensing currents are effected simultaneously with the heating currents, and the measuring means includes filtering means for filtering out the first frequency from the voltage differential whereby the voltage differential is a filtered signal representative of differential temperature between the resistance elements.

11. The apparatus of claim 10 further comprising differential heating means for causing a difference in heating between the resistance elements to thereby effect the voltage differential in producing the filtered signal, the first current means being receptive of the filtered signal to generate a corresponding current differential between the heating currents, so as to compensate for the difference in heating and thereby reduce the voltage differential.

12. The apparatus of claim 11 wherein the differential heating means comprises each resistance element being positionable proximate a different one of two sample materials so as to supply heat thereto, such that the filtered signal provides a measure of differential temperature between the sample materials.

13. The apparatus of claim 11 wherein the heating currents induce heating voltages respectively across each resistance element, and the apparatus further comprises means for measuring an average voltage of the heating voltages, and means for computing a multiplication product of the average voltage and the current differential as a measure of incremental power utilized to compensate for the difference in heating.

14. The apparatus of claim 11 wherein half of the current differential is applied as a positive current increment to one of the resistance elements, and half of the current differential is applied as a negative current increment to another of the resistance elements.

15. The apparatus of claim 11 further comprising averaging means for averaging voltages on the resistance elements to produce a feedback signal, and wherein the first current means comprises a high impedance current source for the heating currents, and control means for comparing the feedback signal and a reference signal to generate an error signal, the current source being receptive of the error signal and the filtered signal to effect the heating currents, one of the heating currents being a sum of a base current and a positive current increment, another of the heating currents being a sum of the base current and a negative current increment, the base current being representative of the error signal, and each current increment being equal in magnitude to half of the current differential.

16. The apparatus of claim 15 wherein the averaging means averages the sensing voltages and filters out the first frequency therefrom to produce the feedback signal representing an average of the sensing voltages.

17. The apparatus of claim 10 wherein the first frequency is substantially zero such that the heating currents are substantially DC, and the second frequency is at least about 100 Hz.

18. The apparatus of claim 10 wherein the second current means comprises a bridge circuit that includes the resistance elements.

19. The apparatus of claim 10 wherein the sensing currents are substantially less than the heating currents.

20. The apparatus of claim 10 wherein the first current means comprises a high impedance current source for each of the heating currents.

21. The apparatus of claim 20 wherein the current source comprises, for each associated resistance element:

a voltage-to-current transducer having a current output terminal, a positive input terminal with a first input resistor extending therefrom, and a negative input terminal with a second input resistor extending therefrom, the first and second input resistors being substantially equal;

control means for applying a control voltage across the first and second input resistors;

a monitor resistor connected between the output terminal and a current output point;

a first feedback resistor connected between the output terminal and the negative input terminal; and a second feedback resistor connected between the output point and the positive input terminal, the first and second feedback resistors being substantially equal, the feedback resistors and the input resistors each being substantially greater than the monitor resistor, and the current output point being connected to the associated resistance element so as to effect the selected heating current therein responsive to the control voltage.

22. The apparatus of claim 21 wherein the transducer consists essentially of an operational amplifier with an inverting input constituting the positive input terminal and a non-inverting input constituting the negative input terminal.

23. The apparatus of claim 21 wherein the transducer comprises a PNP transistor with a positively biased base and a collector constituting the output terminal, and an operational amplifier with a non-inverting input constituting the positive input terminal, an inverting input constituting the negative input terminal, and an amplifier output resistively connected to the biased base.

24. The apparatus of claim 21 wherein the current from the associated resistance element is communicated to a base terminal, and the apparatus further comprises a pair of substantially equal grounding resistors each being connected between a different one of the input terminals and the base terminal and being substantially greater than the monitor resistor.

25. The apparatus of claim 10 wherein the heating currents induce respective heating voltages across the resistance elements, the apparatus further comprises differential heating means for causing a difference in heating between the resistance elements to thereby effect the voltage differential in producing the filtered signal, and the first current means comprises a high impedance current source for the heating currents, averaging means for averaging the sensing voltages to produce a feedback signal representing an average of the sensing voltages, and means for comparing the feedback signal and a preset signal to generate a base signal, the current source being receptive of the base signal and the filtered signal to effect the heating currents, one of the heating currents being a sum of a base current and a positive current increment, and another of the heating currents being a sum of the base current and a negative current increment, such that the base current is representative of the base signal, and the current increments are equal in magnitude to each other so as to compensate for the difference in heating and thereby reduce the voltage differential.

* * * * *

UNITED STATES PATENT AND TRADEMARK OFFICE
CERTIFICATE OF CORRECTION

PATENT NO. : 5,098,196
DATED      : March 24, 1992
INVENTOR(S) : Michael J. O'Neill It is certified that error appears in the above-identified patent and that said Letters Patent is hereby corrected as shown below:

Column 7, line 64, after "similarly", insert --converted--

Column 7, line 65, after "(ADC)", delete --converted--

Column 8, line 2, after "$2^{17}$", insert --counts per second--

Column 8, line 3, after "converter", insert --(DAC)--

Signed and Sealed this

Sixth Day of July, 1993

MICHAEL K. KIRK

Attest:

Attesting Officer

Acting Commissioner of Patents and Trademarks